(12) United States Patent
Shah et al.

(10) Patent No.: US 9,180,072 B2
(45) Date of Patent: Nov. 10, 2015

(54) SEALBIO: A NOVEL NON-OBTURATION REGENERATIVE TECHNIQUE OF ENDODONTIC TREATMENT

(75) Inventors: Naseem Shah, New Delhi (IN); Ajay Logani, New Delhi (IN)

(73) Assignees: Department of Biotechnology, New Delhi (IN); All Indian Institute of Medical Sciences, New Delhi (IN)

( * ) Notice: Subject to any disclaimer, the term of this patent is extended or adjusted under 35 U.S.C. 154(b) by 145 days.

(21) Appl. No.: 13/390,620

(22) PCT Filed: Jun. 16, 2010

(86) PCT No.: PCT/IN2010/000407
§ 371 (c)(1),
(2), (4) Date: Feb. 15, 2012

(87) PCT Pub. No.: WO2011/158245
PCT Pub. Date: Dec. 22, 2011

(65) Prior Publication Data
US 2012/0231422 A1    Sep. 13, 2012

(51) Int. Cl.
*A61K 6/00* (2006.01)
*A61K 6/06* (2006.01)

(52) U.S. Cl.
CPC ............. *A61K 6/0625* (2013.01); *A61K 6/0035* (2013.01); *A61K 6/0038* (2013.01); *A61K 6/0041* (2013.01); *A61K 6/0643* (2013.01)

(58) Field of Classification Search
CPC .. A61K 6/0038; A61K 6/0041; A61K 6/0643
USPC .................................. 433/8–16, 24, 215, 224
See application file for complete search history.

(56) References Cited

U.S. PATENT DOCUMENTS

| | | | |
|---|---|---|---|
| 3,367,778 A | 2/1968 | Berriman et al. | |
| 4,721,735 A | 1/1988 | Bennett et al. | |
| 5,084,491 A | 1/1992 | Kerby | |
| 7,553,362 B2* | 6/2009 | Lu et al. | 106/35 |
| 7,575,628 B2* | 8/2009 | Lu et al. | 106/640 |
| 2006/0213395 A1* | 9/2006 | Lu et al. | 106/35 |
| 2007/0098811 A1* | 5/2007 | Lu et al. | 424/602 |
| 2007/0207445 A1* | 9/2007 | Pitel | 433/224 |
| 2008/0299093 A1* | 12/2008 | Yang et al. | 424/93.7 |

(Continued)

FOREIGN PATENT DOCUMENTS

| | | |
|---|---|---|
| WO | WO 2006116530 A2 * | 11/2006 |
| WO | WO-2009/078971 | 6/2009 |
| WO | WO 2009078971 A1 * | 6/2009 |

OTHER PUBLICATIONS

Shah et al., Efficacy of Revascularization to Induce Apexification/Apexogensis in Infected, Nonvital, Immature Teeth: A Pilot Clinical Study, 2008, pp. 919-925, vol. 34, No. 8.

(Continued)

*Primary Examiner* — Cris L Rodriguez
*Assistant Examiner* — Hao D Mai
(74) *Attorney, Agent, or Firm* — Venable LLP; Keith G. Haddaway

(57) ABSTRACT

This invention relates to a novel non-obturation, regenerative technique "SealBio" of endodontic treatment involving regenerative potential of stem cells and signaling molecules, locally available in the peri-radicular region of teeth, wherein they are stimulated to induce healing and deposition of a natural barrier (seal) at the root apex.

13 Claims, 1 Drawing Sheet

(56) References Cited

U.S. PATENT DOCUMENTS

Figure 1:
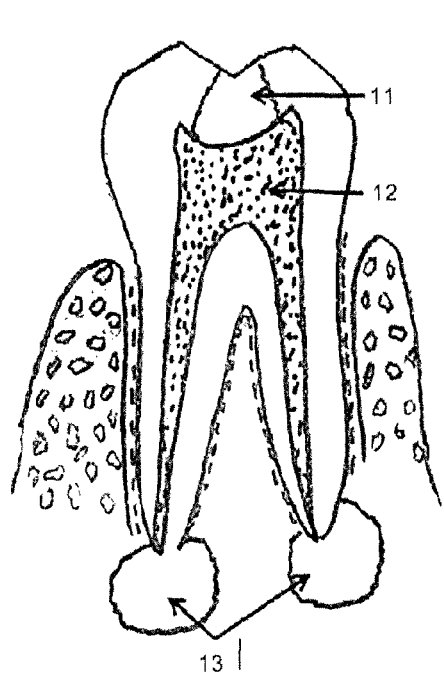

2009/0148486 A1* 6/2009 Lu et al. .................. 424/422
2010/0203481 A1* 8/2010 Murray et al. ............ 433/224

OTHER PUBLICATIONS

Huang, A Paradigm Shift in Endodontic Management of Immature Teeth: Conservation of Stem Cells for Regeneration, 2008, pp. 379-386, Journal of Dentistry 36.

Vasudev SK, Root End Filling Materials-A Review, Endodontology, 2003, pp. 12-18, vol. 15.

Sinha et al., Comparison of Marginal Adaption of Three Retrograde Filling Materials: A Scanning Electron Microscope Study, Endodontology, 1996, vol. 8, No. 2.

International Search Report of PCT/IN2010/000407 filed Dec. 12, 2008.

\* cited by examiner

SEALBIO: A NOVEL NON-OBTURATION REGENERATIVE TECHNIQUE OF ENDODONTIC TREATMENT

FIELD OF INVENTION

This invention relates to a novel non-obturation, regenerative technique "SealBio" of Endodontic treatment.

BACKGROUND OF INVENTION

Endodontic treatment involves thorough cleaning and shaping of root canal to debride all narcotic tissues and microorganism and complete fluid tight obturation (filling) of the entire root canal system.

Root canal morphology in different teeth is vastly different. Even in the same teeth in the population, the morphology of canal system is diverse. Most of the canals are curved. There is presence of extra canals, lateral and accessory canals, cul-de-sac etc. Filling the total root canal space to provide fluid-tight seal is a challenge. There are also several controversies regarding the ideal level of termination of root canal filling—whether to keep it flush with radiographic apex or to keep it 1 mm, short of the apex. The level of filling recommended is different in different clinical cases; whether the pulp was vital or non-vial at the start of the treatment, whether there was periapical pathology, diagnosed clinically or radiographically, whether alveolar bone and/or root resorption was present etc. Also, if apical constriction is not present as in cases of wide open apex and apical root resorption, achieving a perfect seal at the apex becomes almost impossible and involves additional steps of placing a biocompatible barrier material first and then obturating the canals. Then there are controversies whether over-extended (extruded) sealer cement is desirable or causes adverse reaction.

To meet all these challenges, a plethora of root canal obturating materials as well as instrument systems has been developed over the years. Each of these systems is technique sensitive and demands precision and adequate training to be able to use it efficiently, besides being expensive. The obturating material has to adapt as close to canal walls as possible, preferably bond with the walls and hence adequate pre-conditioning of canal walls as well as sealer cement is required. Use of all these material also involves safety and biocompatibility with the tissues. Hence, a non-obturation method of endodontic treatment of non-vital, infected teeth is highly desirable.

The technique of "non-obturation, regenerative endodontic treatment" will greatly simplify the endodontic treatment. The technique is based on regenerative potential of stem cells, locally available in the peri-radicular region of teeth, which are stimulated to induce healing and deposition of a natural barrier (seal) at the root apex, eliminating the need for cumbersome obturation process.

Endodontic literature states that approx. 60% of endodontic failures are due to inadequate obturation of root canal system. Therefore, if the step of obturation is eliminated altogether, the endodontic treatment is simplified to a large extent. The technique is simple, highly cost effective and has the potential to achieve periapical healing.

The technique involves recruiting stem cells and growth factors from the periapical region to affect healing and regeneration. If proved effective, this study can trigger further research in regenerative therapies in Endodontics in particular and in Dentistry in general.

This procedure is a novel procedure which was conceived by going through extensive literature search and our own previous clinical study on "Revascularization for inducing apexogenesis/apexification in non-vital, immature permanent incisors: a pilot study" which is published in Journal of Endodontics, a highly acclaimed International Journal on Endodontics. (Shah N, Logani A, Bhasker U and Aggarwal V. Revascularization for inducing apexogenesis/apexification in non-vital, immature permanent incisors: a pilot study. *J. Endod.* 2007; 34: 919-925.

In this study, stem cells i.e., BMMSC, PDLSC, DPSC were stimulated by over-instrumentation into the periapical tissues through the root canal in immature, non-vital infected teeth. Over-instrumentation induced bleeding into the canal which was allowed to form a clot, into which the new capillaries and stem cells could proliferate. Various growth factors like PDGF, VEGF etc. from blood, bone marrow and dentin affect differentiation of these stem cells into fibroblasts, cementoblasts, osteoblasts etc. which lay down collagen fibrils and hard tissues in the form of cementum, bone, osteodentin etc. The results of this study indicated that recruitment of locally available stem cells not only deposited the hard tissue at the apical end (affecting apical seal) but also on thin lateral dentinal walls and even elongation of root i.e. complete maturation of poorly developed root. Based on the very encouraging results in immature teeth, where periapical healing and tissue regeneration was achieved in immature teeth without root canal obturation, it was conceived to test the process in fully developed mature teeth, adhering to the principles of elimination of root canal infection by thorough cleaning and shaping of root canals and proper sealing of the coronal cavity.

Occasional cases in dental literature have shown that periapical infection will heal following thorough debridement and infection control in the root canal system even without obturation of root canals. An experimental animal study reported in 2006 from UCLA tested the outcome of endodontic treatment with and without obturation of root canal system and found no significant difference in healing, proven by histology of peri-radicular tissues.

The existing modern endodontic treatment requires that root canal system be completely disinfected and obturated in three dimensions to achieve a fluid tight seal of the root canal system. In recent past, importance of coronal seal is realized to be as important as apical seal to prevent micro-leakage, bacterial ingress and re-infection of the canal system and periapical tissues.

To achieve these objectives, a very systematic, exacting and highly technical procedures are established. Not only the root canal system need to be chemo-mechanically prepared to disinfect the canal system, it also needs to be shaped to receive and compact the obturating material in three dimension to a specific apical limit, dictated by several factors like presence or absence of periapical lesion, root resorption etc. The most preferred obturating material till date is gutta percha rolled into different sizes of cones/points and is being used with sealer cement. There are several techniques of obturation such as lateral and vertical condensation, thermoplasticised Gutta percha obturation, thermo-mechanical compaction, injectable gutta percha filling etc. Each of these obturation systems require that canal be shaped according to the type of obturating technique to be followed. In addition, there are several sealer cements being used, each with its own advantages and limitations and biocompatibility behavior. More recently, resin based obturating materials and sealers are promoted to achieve bonding with the root canal walls. After root canal obturation, coronal seal is given in the form of a restoration or crown to prevent future re-infection.

The case requires regular follow up at an interval of 6 months till at least 2 yrs to categorize the healing as good, satisfactory or poor, both by clinical and radiographic method.

Root canal obturation is an exacting technique, demanding rigorous training and clinical skills. Each of the obturation technique and system (obturation equipments) require canals to be prepared accordingly. A large inventory of obturation systems and materials is required to obturate different canal systems. All these factors put increased demand on operators' skill and time and finally increase the cost of treatment. Also, as it increases the treatment time, only a few teeth from amongst those requiring endodontic treatment can be treated, the rest being condemned to extraction. (Loss of tooth).

All the above drawbacks are overcome by the new treatment approach proposed, i.e. achieving a biological seal rather than mechanical seal obtained by artificial obturating materials, the "Non-obturation endodontic treatment". It not only dispenses with root canal obturation step with all its drawbacks, it simplifies the endodontic treatment, reduces the treatment time and ultimately reduces the cost of treatment. This new technique would provide the clinician an opportunity to save more number of pulp and periapically involved teeth, which otherwise would have been lost to extraction.

Another significant advantage of this novel treatment approach is its significant contribution towards understanding the role of stem cells and signaling molecules in healing mechanism of periapical pathologies, regeneration of damaged tissues and achieving biological seal (SealBio) at the root apex, by recruiting indigenous, locally available stem cells and growth factors. This technique can trigger further research in tissue engineering for repair and regeneration in other oral pathologies in future.

OBJECTIVES OF INVENTION

The main objective is to develop a simple endodontic treatment protocol for pulp and periapically involved teeth to reduce the demand on time, technique sensitivity and cost of treatment.

Other objective is to develop a technique based on regenerative principles wherein healing of periapical pathological lesions is hastened, recruiting indigenous, locally available stem cells.

Another objective is to develop a regenerative technique wherein biomodulation can be done without additional cost of biomaterials such as collagen, calcium phosphate cement, mineral trioxide aggregate, hydroxyl apatite etc.

Further objective is to develop a technique that eliminates the need for root canal fillings.

Other objective is to develop a technique which deals with a successful biological seal rather than mechanical seal.

STATEMENT OF INVENTION

This invention relates to a novel non-obturation, regenerative technique SealBio of endodontic treatment involving regenerative potential of stem cells and signaling molecules, locally available in the peri-radicular region of teeth, wherein they are stimulated to induce healing and deposition of a natural barrier (seal) at the root apex comprising the steps of canal cleaning, specially the apical third of the canal, establishing apical patency with #10 reamer to prevent clogging of apical foramen with debris, irrigating canals thoroughly with sodium hypochlorite and stimulating the stem cells and growth factors in the apical region of the root. After confirming the apical patency with size #10 reamer and then gradually to widened size #15, taking a fresh #15 size sterile reamer 2-3 mm past the apical foramen and gently rotating clock wise, giving 2-3 turns, withdrawing reamer giving anti clock wise rotation, introducing a sub base of zinc oxide eugenol (Kalsogen) in the access introducing a sub base of zinc oxide eugenol (Kalsogen) in the access cavity and condensing it with a hand plugger in to the cervical ⅓ of root canals, placing a base of Zn-phosphate cement and giving silver amalgam restoration after application of cavity varnish at the same sitting.

BRIEF DESCRIPTION OF ACCOMPANYING DRAWINGS

FIG. 1. A diseased tooth with periapical pathology (11, dental caries, 12, infected nonvital pulp, 13, bone resorption).

Figure 2:
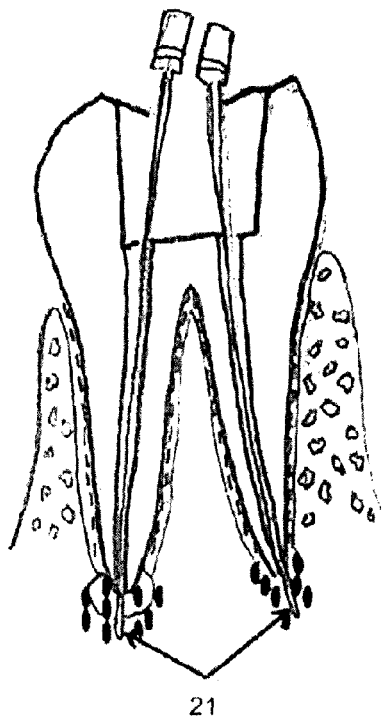

FIG. 2. Intentional over-instrumentation into the periapical region after thorough disinfection of the canals (21, over instrumentation and stimulation of stem cells).

Figure 3:
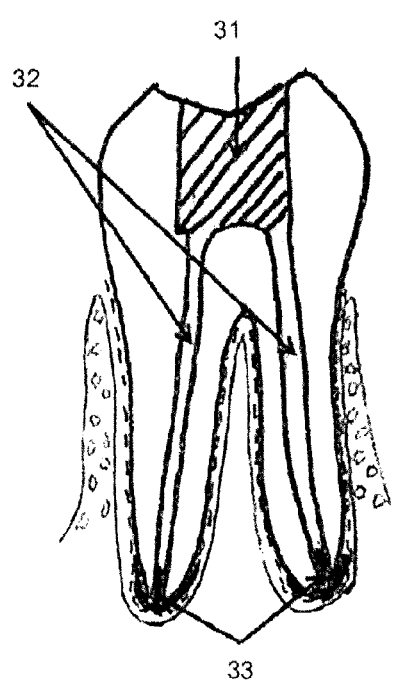

FIG. 3. A fluid-tight coronal seal and deposition of apical mineralized tissue—"SealBio" (31, coronal fluid-tight seal, 32, disinfected clean canals, 33, biological seal "SealBio" at the apical foramen).

DETAILED DESCRIPTION OF INVENTION

It is for the very first time that a non-obturation endodontic treatment in fully formed mature teeth in pulp and periapically involved (diseased) teeth is being proposed. Endodontic textbooks and literature is voluminous on merits of different techniques, equipments, and materials for root canal fillings. Plethora of studies is done on success and failure of endodontic treatment as related to level and quality of obturation of root canals. But so far, none has proposed a technique which dispenses with the need for root canal obturation.

Hence, it is a very novel treatment approach conceived after our success with similar treatment protocol and justification in immature teeth and extensive literature search on the subject.

This approach greatly simplifies endodontic treatment as one of the major three steps of endodontic treatment is not necessary to achieve success. Importance is given to thorough cleaning and disinfection of root canal system, and achieving a perfect coronal seal. This technique would allow saving many more endodontically involved teeth, as it would cut down on cost involved with root canal obturation systems, materials as well as time.

The technique is based on utilizing locally available stem cells and growth factors without any additional laboratory technique or cost of materials involved. Hence, its success can trigger research in regenerative techniques in other clinical situations in Dental Science.

Success of conventional endodontic treatment depends on thorough cleaning, shaping and disinfection of root canal system, followed by fluid tight obturation of root canal system and thoroughly sealing the coronal access, to prevent future re-infection.

In the "non-obturation regenerative method of endodontic treatment", the same regenerative mechanism is expected to occur without obturation of root canal system. The healing cascade of events is stimulated in the periapical tissues, after thorough debridement and disinfection of root canal system. The process stimulates the various stem cells and activates signaling molecules leading to cellular events such as chemotaxis, angiogenesis, proliferation and differentiation of cells and finally regeneration of soft and hard tissues. Hence, a biological seal is achieved at the root apex rather than attempting to seal the apical end with artificial obturating materials with all its drawbacks, i.e.,
  (i) Exacting and demanding technique
  (ii) Additional time
  (iii) Plethora of materials and equipments
  (iv) Chances of over or under filling
  (v) Issue of biocompatibility of various sealers and core materials
  (vi) Possibility of root fracture during root filling procedure Detailed Technique:

Cases of periapical infection, irrespective of age, sex or the tooth involved can be treated by this technique.

After getting the consent of the patient, access opening, cleaning and shaping of root canals is done with hand or rotary Ni—Ti instruments, irrigated with $H_2O_2$ and NaOCl and inter-appointment dressing of non-specific antiseptic CMCP or triantibiotic paste of Metrogyl, ciprofloxacin and tetracycline is given. During canal cleaning, special attention is given to cleaning the apical third of the canal as this part of the canal is known to harbor maximum number of microorganisms. Apical patency is established with #10 reamer to prevent clogging of apical foramen with debris and maintained throughout the cleaning and shaping process.

Depending on the extent of infection, either one or two dressings at one week's interval can be given. When the infection control is achieved, as evident from a clinically symptom-free tooth with dry canals, healed swelling or sinuses etc. the process of achieving "SealBio" is performed.

After removing the inter-appointment dressing, the canals are thoroughly irrigated with NaOCl. The apical patency is again checked with size #10 reamer and then gradually widened to size #15. Once the free access is gained to apical tissues, a #15 fresh, sterile reamer is taken 2-3 mm past the apical foramen and gently rotated clock-wise, giving 2-3 turns. The reamer is then withdrawn giving anti-clock-wise rotation. In cases where large periapical lesion was present at the initiation of treatment, apical root resorption may be present and apical foramen may already be wide. In such cases, even larger size #25 or #30 reamer can be taken past the foramen to stimulate stem cells and growth factors. A sub-base of zinc oxide-eugenol (Kalsogen) is introduced in the access cavity and with a hand plugger, condensed into the cervical $\frac{1}{3}^{rd}$ of the root canals. A base of Zn-phosphate cement is placed and silver amalgam restoration is given after application of cavity varnish at the same sitting.

In cases with extensive crown destruction, a base of cavit, instead of kalsogen, is similarly packed into the pulp chamber and coronal ⅓ of root canals (To prevent contact of Cermet cement with zinc-oxide eugenol, which can adversely affect the properties of Glass-ionomer based Cermet cement). The excess is removed from the walls of the cavity, dentinal walls are pre-conditioned with 10% polyacrylic acid for seconds the core is built with Cermet cement and a full crown restoration is given.

Immediate post-treatment radiograph is taken. The patient is kept under regular follow up follow up to evaluate if there is any complication or recurrence of infection and to monitor the progress of healing. Recall is done at 6 wks, 3 months, 6 months, 1 and 2 years.

We claim:

1. A non-obturation, regenerative endodontic treatment technique for a permanent mature tooth, involving regenerative potential of stem cells and signaling molecules locally available in a periapical region of the tooth, wherein said stem cells are stimulated to induce healing and deposition of a mineralized barrier (biological seal) at a root apex of the tooth, thus eliminating a need for a root canal obturation, comprising the steps of:
  a. widening of apical foramina of the permanent mature tooth's root canals with files larger than an initial apical file (IAF) at working length and irrigating with NaOCl after achieving infection control as evident from a clinically symptom-free tooth with dry canals, healed swelling or sinuses;
  b. introducing or pushing a sterile reamer of size 30 or less to 2-3 mm past said tooth's apical foramina into said tooth's periapical regions and then withdrawing said reamer;
  c. leaving the root canals without filling thus eliminating an obturation step;
  d. introducing calcium sulfate-based cement in an access cavity to cover pulpal floor of the tooth and condensing said calcium-sulfate based cement, with a hand plugger, into a cervical ⅓ of said tooth's root canals for sealing; and
  e. restoring the access cavity with an appropriate permanent restoration to prevent leakage and re-infection of said root canals.

2. The non-obturation, regenerative endodontic treatment technique, as claimed in claim 1, wherein said technique achieves periapical healing.

3. The non-obturation, regenerative endodontic treatment technique, as claimed in claim 1, wherein said technique stimulates said stem cells and activates signaling molecules leading to cellular events of chemotaxis, angiogenesis, proliferation and differentiation of cells and regeneration of soft and hard tissues.

4. The non-obturation, regenerative endodontic treatment technique, as claimed in claim 1, wherein biomodulation is accomplished without use of biomaterials.

5. The non-obturation, regenerative endodontic treatment technique, as claimed in claim 1, wherein said technique is used for endodontic treatment in fully formed mature teeth in pulp and periapically involved teeth.

6. The non-obturation, regenerative endodontic treatment technique, as claimed in claim 3, wherein biomodulation is accomplished without the use of biomaterials.

7. The non-obturation, regenerative endodontic treatment technique, as claimed in claim 3, wherein said technique is used for endodontic treatment in fully formed mature teeth in pulp and periapically involved teeth.

8. The non-obturation, regenerative endodontic treatment technique, as claimed in claim 4, wherein said technique is used for endodontic treatment in fully formed mature teeth in pulp and periapically involved teeth.

9. The non-obturation, regenerative endodontic treatment technique, as claimed in claim 1, wherein widening of apical foramina is performed with files 2-4 sizes larger than the initial apical file (IAF) at working length.

10. The non-obturation, regenerative endodontic treatment technique, as claimed in claim 1, wherein biomodulation is accomplished without the use of collagen, calcium phosphate cement, mineral trioxide aggregate, or hydroxyl apatite.

11. The non-obturation, regenerative endodontic treatment technique, as claimed in claim 3, wherein biomodulation is accomplished without the use of collagen, calcium phosphate cement, mineral trioxide aggregate, or hydroxyl apatite.

12. The non-obturation, regenerative endodontic treatment technique, as claimed in claim 1, wherein a biological seal is formed without mechanical seal at the apical foramen.

13. The non-obturation, regenerative endodontic treatment technique, as claimed in claim 1, wherein the sterile reamer of step (b) is a size #15 reamer.

\* \* \* \* \*